(12) United States Patent
Pentland et al.

(10) Patent No.: US 8,461,082 B2
(45) Date of Patent: Jun. 11, 2013

(54) HERBICIDAL COMPOSITION AND METHOD FOR REMOVING UNWANTED FOLIAGE

(75) Inventors: Philip Edward Pentland, Flemington (AU); Anthony Gerard Flynn, Wandana Heights (AU)

(73) Assignee: Eureka Agresearch Pty Ltd, Victoria (AU)

( * ) Notice: Subject to any disclaimer, the term of this patent is extended or adjusted under 35 U.S.C. 154(b) by 774 days.

(21) Appl. No.: 12/304,538

(22) PCT Filed: Jun. 14, 2007

(86) PCT No.: PCT/AU2007/000832
§ 371 (c)(1),
(2), (4) Date: Feb. 18, 2009

(87) PCT Pub. No.: WO2007/143788
PCT Pub. Date: Dec. 21, 2007

(65) Prior Publication Data
US 2009/0298694 A1    Dec. 3, 2009

(30) Foreign Application Priority Data

Jun. 14, 2006   (AU) ............................... 2006903203

(51) Int. Cl.
*A01N 57/18* (2006.01)
*A01N 25/00* (2006.01)
*A01N 37/00* (2006.01)
*A01N 37/44* (2006.01)
*A01N 47/28* (2006.01)

(52) U.S. Cl.
USPC ........ 504/206; 504/116.1; 504/142; 504/147; 504/148

(58) Field of Classification Search
USPC ....................... 504/206, 116.1, 142, 147, 148
See application file for complete search history.

(56) References Cited

U.S. PATENT DOCUMENTS

| | | | | | |
|---|---|---|---|---|---|
| 5,266,553 | A | * | 11/1993 | Champion et al. | 504/206 |
| 5,635,445 | A | * | 6/1997 | Schapira et al. | 504/127 |
| 5,798,310 | A | * | 8/1998 | Toussaint et al. | 504/206 |
| 5,994,271 | A | * | 11/1999 | Ravetta et al. | 504/206 |
| 6,479,434 | B1 | * | 11/2002 | Gillespie et al. | 504/206 |

(Continued)

FOREIGN PATENT DOCUMENTS

| | | |
|---|---|---|
| AU | 10067/97 C | 7/1997 |
| AU | 725067 B | 10/2000 |

(Continued)

OTHER PUBLICATIONS

H. Erdal Ozkan, "Boom Sprayer Calibration" (1992), Ohio State University Extension; Food, Agricultural and Biological Engineering, Columbus, Ohio (http://ohioline.osu.edu/aex-fact/0520.html).*

(Continued)

*Primary Examiner* — Jane C Oswecki
(74) *Attorney, Agent, or Firm* — Norris McLaughlin & Marcus PA

(57) ABSTRACT

This invention relates to a method of preparing a spray tank mix of glyphosate comprising (a) providing glyphosate acid concentrate; (b) providing an alkaline composition; and (c) forming a mixture of glyphosate acid concentrate and alkaline composition in the spray tank by addition of a composition comprising the glyphosate acid concentrate to a diluted aqueous mixture of the alkaline composition.

16 Claims, 3 Drawing Sheets

Comparison of the efficacy of a 2 Pack glyphosate system and "Roundup Biactive"™ herbicide on the fresh wt of annual ryegrass (*Lolium rigidum*)

U.S. PATENT DOCUMENTS

| | | | |
|---|---|---|---|
| 6,645,912 B1 * | 11/2003 | Mille et al. ............... | 504/206 |
| 6,992,046 B2 * | 1/2006 | Bramati et al. ............ | 504/206 |
| 2005/0032649 A1 | 2/2005 | Tank et al. | |

FOREIGN PATENT DOCUMENTS

| | | | |
|---|---|---|---|
| IE | 64134 B3 | | 7/1995 |
| IE | 940037 B3 | * | 7/1995 |
| IE | 940037 | * | 12/1995 |
| WO | 00/67571 A1 | | 11/2000 |
| WO | 01/26463 A1 | | 4/2001 |
| WO | 03/013241 A1 | | 2/2003 |
| WO | 03/063589 | * | 8/2003 |
| WO | WO03063589 A2 | * | 8/2003 |

OTHER PUBLICATIONS

T.L. Wiles and D. G. Sharp, "International Code of Conduct on the Distribution and Use of Pesticides", 2001, Food and Agriculture Organization of the United Nations, vol. Two, pp. 1-20.*

Wiles and Sharp, "International Code of Conduct on the Distribution and Use of Pesticides", 2001, Food and Agriculture Organization of the United Nations, vol. Two, pp. 1-20 (previously supplied).*

T.L. Wiles and D.G. Sharp, "International Code of Conduct on the Distribution and Use of Pesticides," 2001, Food and Agriculture Organization of the United Nations, vol. Two, pp. 1-20.*

* cited by examiner

Figure 1. Comparison of the efficacy of a 2 Pack glyphosate system and "Roundup Biactive"™ herbicide on the fresh wt of annual ryegrass (*Lolium rigidum*)
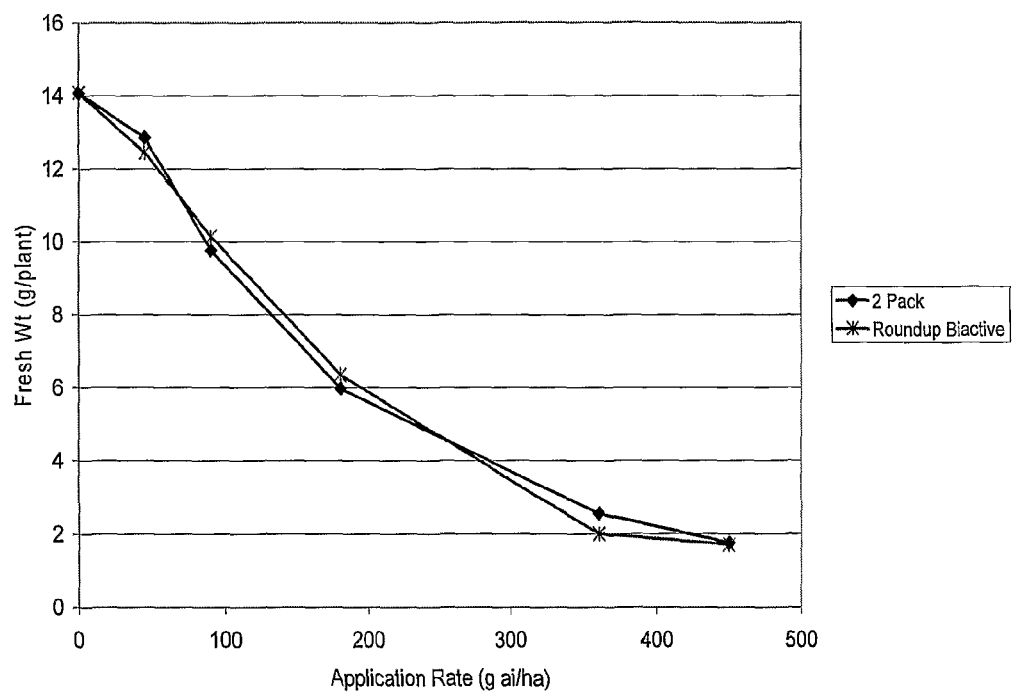

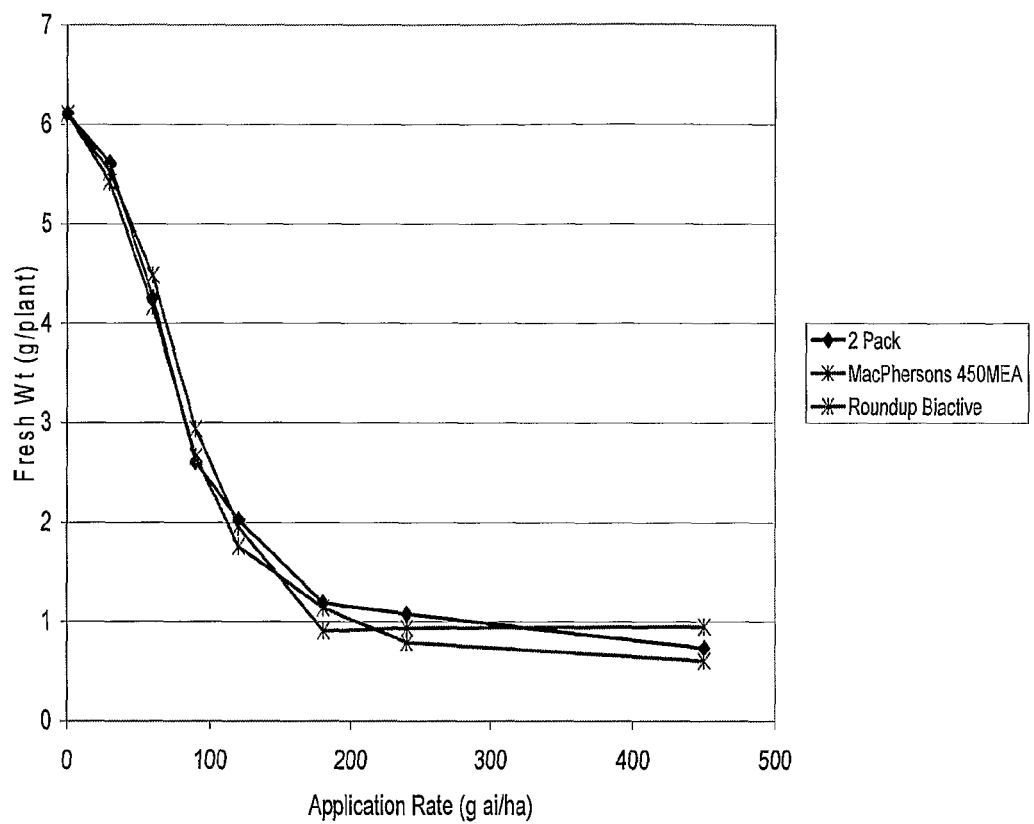
Figure 2. Comparison of the efficacy of glyphosate treatments on the fresh wt of oats (*Avena sativa*)

Figure 3  Comparison of the efficacy of a 2 Pack glyphosate system and "Roundup Biactive"™ herbicide on the density of annual ryegrass (*Lolium rigidum*) in a field trial near Werribee, Victoria, Australia
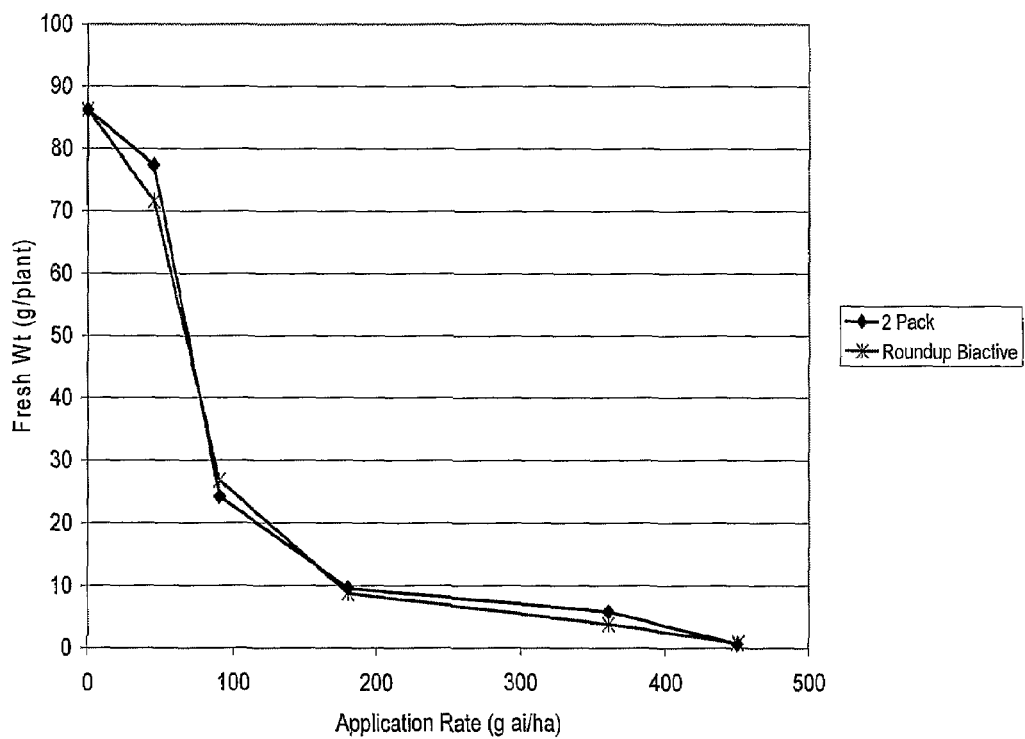

HERBICIDAL COMPOSITION AND METHOD FOR REMOVING UNWANTED FOLIAGE

This is an application filed under 35 USC 371 of PCT/AU2007/000832.

FIELD

This patent relates to herbicidal formulations and to their use in removing unwanted foliage. In particular the invention relates to a composition and method of use of the herbicide glyphosate.

In current practice the weed-killer glyphosate is transported to the ware-house of the distributor, and from thence to the farm or other site of application most commonly as a concentrate liquid aqueous formulation containing glyphosate in the form of a salt such as the isopropylamine or ammonium salts. In the manufacture of glyphosate the acid form is precipitated from the reaction mixture and the resulting wet cake is reacted with the appropriate base to form a water soluble salt. The intermediate glyphosate technical grade acid is poorly water soluble and not generally useful as an herbicide. The herbicidal composition of salts of glyphosate is then prepared from the salt as an aqueous solution concentrate and may contain adjuvants such as a surfactant that reinforces the herbicidal effect of glyphosate.

The preparation of glyphosate as an aqueous concentrate of glyphosate salts necessarily entails disadvantages, such as the need to transport larger than necessary weights or volumes of prepared glyphosate salt liquor, the need to dispose of contaminated, rigid packaging materials, the danger that spilling the prepared glyphosate salt liquor prior to its addition to the spray tank will create environmental damage, and the cost penalties associated with using robust packaging materials, and with the processing step of salt-formation.

U.S. Pat. No. 6,475,954 (Hamroll et al. filed Oct. 2, 2001) teaches the application of glyphosate acid (as distinct from glyphosate salt) in a composition which further comprises a carbonate or bicarbonate, organic acid chosen from citric, oxalic and adipic acids, hydrosoluble cellulose, a glyphosate-synergising surfactant, and a bonding agent such as ammonium or sodium sulphate or urea. The formulations are generally presented as a tablet for addition to water, for convenient dispensing by small-scale users. Carbon dioxide is generated as a result of the acid-carbonate reaction to facilitate rapid disintegration of the tablet. Submerging the composition in water causes the glyphosate acid to convert into a soluble salt and solubilises the glyphosate by the formation of the salt. The teachings of this patent are not useful when weed control is required over a large area because the deposition of a large number of tablets into a large spray tank and the resultant foaming is not practical for broad acre use.

U.S. Pat. No. 5,118,338 describes a composition containing glyphosate acid solid powder or granules which are formulated using a very specific surfactant having a chain length of 16 to 18 carbon atoms and 25 units of ethylene oxide and an HLB of about 16. The surfactant is said to be very important to the success of the formulation.

U.S. Pat. No. 6,746,988 (Hopkinson et al; filed Sep. 5, 2002) teaches an agricultural composition comprising at least one agriculturally active compound (which may be glyphosate in salt form). This composition also comprises at least one alkyl polyglycoside, at least one anionic surfactant (selected from the set polyarylphenolpolyalkoxyether sulphate and polyarylphenolpolyalkoxyether phosphate) and at least one basic compound wherein the at least one anionic surfactant is neutralised to the inflection point in the titration curve with the at least one basic compound. Preferred basic compounds are selected from the set tallowamine ethoxylate, cocoamine alkoxylate, oleylamine alkoxylate, stearylamine alkoxylate, linoleic diethanolamide. The basic compounds are preferably present in an amount of 0.1 to 8% by weight, more preferably in an amount of 0.5 to 4% by weight. U.S. Pat. No. 6,746,988 teaches a preference that anionic surfactants and basic compounds are in a ratio of about 1:1. The preferred range for anionic surfactants in the composition is 0.1 to 8% by weight, more preferably 1-4%. The above formulation is a complex, multi-component formulation and is designed to provide robust in-tank performance for many different active ingredients. These formulations are intended for use as a one-pack formulation which includes the agriculturally active compound.

U.S. Pat. No. 6,207,617 (Gillespie J, filed April 1999) assigned to Monsanto teaches a concentrate composition of a plant treatment compound in acid form, wherein the plant treatment compound has a solubility in deionised water at 25 deg C. of less than about 50 g/l and is present predominantly in the acid form. The composition further comprises an ethoxylated aliphatic hydrocarbon surfactant wherein the hydrocarbon has about 24 to 60 carbon atoms and the number of ethoxy moieties is about 5 to about 100. The plant treatment compound can be glyphosate. The weight ratio of surfactant to plant treatment compound, expressed as acid equivalent, is about 1:2 to 1:30. This invention is limited to one-pack formulations wherein all components of the plant treatment compound are contained in one pack. The surfactant is not a standard surfactant for herbicidal formulations.

Two pack formulations of glyphosate have also been proposed. Nufarm of Pipe Road Layerton, Victoria, Australia have sold "Credit plus Bonus", wherein one pack (Credit) comprises glyphosate salt (in fact a dual salt, more particularly isopropylamine and mono-ammonium salts) and the other pack (Bonus) comprises adjuvant described as a proprietary blend of surfactants, acidifiers and water conditioners. The two packs are added to the spray tank in a 1:1 ratio.

The UGA Cotton Newsletter of Apr. 26, 2000 provides a table of glyphosate products together with adjuvant recommendations (provided as a separate component to the spray tank). Products in this table include products by BASF, Nufarm, Cheminova, Dow, Griffin LLC, Helena, Monsanto, Dupont and Zeneca. The products invariably comprise a glyphosate salt (generally isopropylamine salt but occasionally ammonium or trimethylsulfonium or other salts) and the common adjuvants are ammonium sulphate (AMS) and/or non-ionic surfactant.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

There is a need for improved glyphosate formulation systems and methods which allow the active to be transported in a highly concentrated form without the requirement or cost of specialist surfactants and additives.

SUMMARY

A method of preparing a spray tank mix of glyphosate comprising
(a) providing a glyphosate acid concentrate;
(b) providing an alkaline composition; and (c) forming a dilute mixture of glyphosate acid concentrate and alkaline composition in the spray tank by addition of a composition comprising the glyphosate acid concentrate to a diluted aqueous mixture of the alkaline composition. The composition may be directly applied to plants from the spray tank.

The glyphosate acid concentrate is preferably a solid particulate material which typically contains at least 50% by weight glyphosate acid (preferably at least 50% and most preferably at least 95% glyphosate acid). This significantly reduces the expense and problems of transport and handling.

An aqueous dispersion of the glyphosate acid concentrate is generally mixed with an aqueous mixture containing the alkaline composition.

In a further embodiment the invention provides a glyphosate formulation system for preparing a glyphosate spray tank mixture the system comprising a pack comprising a glyphosate acid concentrate composition for addition to a spray tank and a pack comprising a water soluble alkaline for reaction with the glyphosate acid in the spray tank to form a water soluble salt thereof in situ.

It is particularly preferred to add the glyphosate acid as a dispersion formed from the glyphosate acid concentrate to the alkaline composition which has been dispersed in water in the spray tank.

Throughout the description and the claims of this specification the word "comprise" and variations of the word, such as "comprising" and "comprises" is not intended to exclude other additives, components, integers or steps.

DETAILED DESCRIPTION

One aspect of the invention provides a method of preparing a spray tank mix of glyphosate comprising
(a) providing a glyphosate acid concentrate;
(b) providing an alkaline composition; and
(c) forming a mixture of glyphosate acid concentrate and alkaline composition in the spray tank by addition of a composition comprising the glyphosate acid concentrate to a diluted aqueous mixture of the alkaline composition.

The invention also provides a method of controlling vegetation comprising the additional step of applying the resulting mixture to plants from the spray tank. The process generally involves dilution of at least one of the components with water to form a dilute composition suitable for application to plants.

In one embodiment the invention provides a method of preparing a spray tank mix of glyphosate comprising:
(a) providing a glyphosate acid concentrate;
(b) providing an alkaline composition;
(c) diluting the alkaline composition with water in the spray tank to provide a diluted alkaline mixture;
(d) adding a composition comprising the glyphosate acid concentrate, optionally diluted with water, to the dilute alkaline mixture; and
(e) optionally adding further water to the spray tank to provide the desired volume.

Glyphosate Acid Concentrate

The invention utilises glyphosate acid which term is used herein to mean N-phosphonomethyl glycine in the form of the free acid as distinguished from the highly water soluble salts such as the isopropyl amine, ammonium and potassium salts which are presently used in glyphosate compositions.

The invention is concerned with preparation of a spray tank mix. Spray tank mixes are prepared in the industry to provide dilution of a herbicidal concentrate, which is sold for farm use, to provide an aqueous mixture having the concentration of pesticide required for application at the site of use by spraying. The concentrate is combined with a diluent, generally water, shortly before use and may be mixed with adjuvants to enhance performance. In contrast to conventional glyphosate concentrates which are based on a salt of glyphosate the present invention utilises a concentrate in the form of glyphosate acid. The concentrate preferably contains glyphosate in the form of particles or granules. The particles may be in the form of an aqueous dispersion or may be adapted to be agitated to provide an aqueous dispersion. Alternatively and more preferably the particulate glyphosate is in the form of dry solid particles.

While a wide range of particle sizes may be used the glyphosate acid concentrate is preferably in the form of a finely divided solid comprising particles of size in the range of from 50 microns to 5 mm, preferably 0.01 mm to 2 mm and most preferably 0.05 mm to 1.5 mm.

The glyphosate acid concentrate may comprise fillers, additives or adjuvants if desired. It is preferred that the glyphosate concentrate is a particulate material comprising at least 50% by weight glyphosate acid, more preferably the glyphosate acid concentrate comprises at least 80% by weight glyphosate acid, still more preferably at least 95% glyphosate acid and most preferably the glyphosate acid concentrate consists essentially of glyphosate acid.

The glyphosate acid concentrate is preferably dry although it will be understood that dry particles may contain some residual water. Accordingly the glyphosate acid concentrate is typically in the form of particles of than 25% preferably less than 20% more preferably less than 15% still more preferably less than 10% more preferably less than 8% by weight water and most preferably less than 5% water.

The invention utilises an alkaline component which preferably forms a water soluble salt with glyphosate on mixing with the glyphosate acid.

The alkaline composition may contain one or more of a wide range of alkaline materials. It is particularly preferred that the alkaline composition contain at least one material selected from the group of alkaline materials registered for use with glyphosate, for example alkali metal bases such as sodium hydroxide and potassium hydroxide, alkananolamines such as monoethanolamine, diethanolamine, triethanolamine and monoisopropanolamine, alkylamine alkoxylates particularly fatty amine ethoxylates such as tallowamine ethoxylate and amines such as alkyl amines including isopropylamines. The most preferred alkaline materials are selected from mono and dialkanolamines and alkyl alkanolamines. Specific examples of preferred alkaline materials include monoethanolamine, isopropanolamine, diethanolamine, triethanolamine and mixtures thereof.

The alkaline composition may, and preferably will contain an adjuvant particularly a surfactant. The preferred surfactants are those which enhance spray performance and or the activity of glyphosate. The surfactant may be of a type registered for use with glyphosate. It is preferred that the alkaline composition comprises a surfactant chosen from the group consisting of amidoaliphaticbetaines, alkylamine alkoxylates particularly fatty amine ethoxylates such as tallowamine ethoxylates, cocobetaine, alkoxylated aliphaticamines, alkylpolyglucosides, alkylglycosides, aliphaticamines quaternary amines, aliphatic acetates, ethylene diamine ethoxylates, amphoteric surfactants such as polyoxyethylene aliphaticamine oxides and polyoxyethylene aliphatic ether salts, amine oxides and amphoacetates. The term aliphatic is used to include saturated as well as unsaturated hydrocarbon chains, and includes linear and branched chains. Glyphosate-synergising surfactants typically contain at least one aliphatic group containing 8 to 22, more frequently 12 to 18 carbon atoms. Discussions of glyphosate-synergising surfactants are provided in U.S. Pat. No. 6,207,617, WO 95/16351, US Pub 20030158042, US Pub 20050170965 and US Pub 20040224846 the contents of which are herein incorporated by reference. The preferred surfactants are selected from aliphatic, betaines amidoaliphaticbetaines and tallow amine ethoxylates.

Betaine surfactants are generally of formula I:

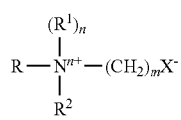

Wherein: R is the aliphatic group of from 1 to 30 carbon atoms or aliphatic amidoalkyl and preferably containing more than 13 carbon atoms; $R^1$ and $R^2$ are each, independently, hydrogen $C_1$ to $C_6$ alkyl or $C_1$ to $C_6$ hydroxyalkyl and preferably is an ethyl, hydroxyethyl or most preferably a methyl group; m is 1 or 2; X is a phosphono, sulphono, or, preferably, carboxy group; and n is 0 or, preferably 1.

R preferably has from 14 to 25 carbon atoms and is desirably a straight chain alkyl or alkyl amido alkylene group, especially a group of the formula $CH_3(CH_2)_aCONH(CH_2)_b$ where (a+b) is from 12 to 23 and b is preferably 2 or most preferably 3.

In one embodiment, the betaine surfactant is a compound according to formula II preferably of formula IIa

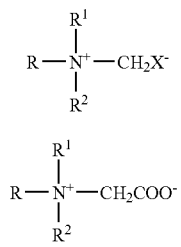

wherein:

R is alkyl, alkenyl, or alkylamidoalkyl, and $R^1$ and $R^2$ are each independently ($C_1$ to $C_6$)alkyl or hydroxy($C_1$ to $C_6$)alkyl.

As used herein, "alkyl" means a saturated straight or branched chain hydrocarbon radical, typically a ($C_1$-$C_{30}$) saturated straight or branched chain hydrocarbon radical, such as for example selected from the group consisting of methyl, ethyl, n-propyl, iso-propyl, n-butyl, sec-butyl, t-butyl, pentyl, n-hexyl, cyclohexyl, octyl, decyl, dodecyl, tetradecyl, hexadecyl, octadecyl, eicosyl, behenyl and tricosyl.

As used herein, the term "alkenyl" means an unsaturated straight chain, branched chain, or cyclic hydrocarbon radical having at least one carbon-carbon double bond per radical, preferably having from $C_2$ to $C_{30}$ alkenyl such as for example, propenyl, butenyl, octadecenyl.

As used herein, "alkylamidoalkyl" means a group according to formula III:

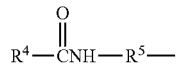

wherein $R^4$ is alkyl or alkenyl, typically ($C_1$ to $C_{30}$)alkyl, and $R^5$ is an alkylenyl radical, typically ($C_1$ to $C_{30}$)alkylenyl and includes, for example, dodecylamidopropyl, cocoamidopropyl and tetradecylamidoethyl.

As used herein, "hydroxy($C_1$ to $C_6$)alkyl" means a hydroxyalkyl group having from 1 to 6 carbon atoms per group, such as for example hydroxymethyl, hydroxyethyl, hydroxypropyl, hydroxybutyl, hydroxypentyl, and hydroxyhexyl. Suitable betaine surfactants include for example, ($C_{12}$ to $C_{18}$) alkyldimethyl betaine, cocoamidopropyl betaine, and mixtures thereof.

In one embodiment, the betaine surfactant comprises a ($C_{12}$ to $C_{16}$) alkyldimethylbetaine.

A particularly preferred surfactant component for use in the alkaline composition comprises an alkylbetaine surfactant, preferably cocobetaine.

Other surfactants which may be used include ethoxylated alkyl amines and alkyl amines.

The alkyl amines (also referred to as fatty amines) or ethoxylated alkyl/fatty amines can comprise at least one hydrocarbon group containing 2 to 24 carbon atoms, optionally polyalkoxylated.

The fatty amines or alkoxylated fatty amines can more particularly be selected from amines comprising at least one linear or branched, saturated or unsaturated group containing 2 to 24 carbon atoms, preferably 8 to 18 carbon atoms, optionally comprising 2 to 30 oxyethylene groups and or polypropylene groups, or a mixture of a plurality thereof. Examples include ethoxylated tallow amines.

The fatty amines or ethoxylated fatty amines can be selected from ethoxylated fatty amines comprising at least one linear or branched, saturated or unsaturated groups containing 6 to 24 carbon atoms, preferably 8 to 20 carbon atoms, comprising 2 to 30 oxyethylene groups, or a mixture of a plurality thereof. Examples include the compounds having the following formula IV:

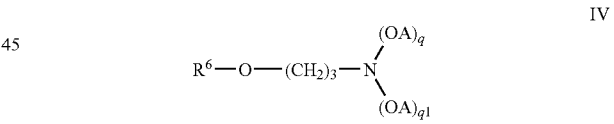

wherein $R^6$ represents a linear or branched, saturated or unsaturated hydrocarbon group containing 6 to 24 carbon atoms, preferably 8 to 20 carbon atoms; OA represents an oxypropylene group; and q, $q^1$, which may or may not be identical, represent a mean number in the range 1 to 30. Examples of such amines that can be cited are amines derived from copra and containing 5 oxyethylene (OE) motifs, oleic amines containing 5 OE, amines derived from tallow containing 5-20 OE, for example 10, compounds corresponding to the above formula, in which $R^6$ is an alkyl group containing 12 to 15 carbon atoms, the number of OE motifs being in the range 20 to 30.

Examples of alkyl amine and ethoxylated alkyl amine surfactants include amine oxide surfactants such as:

an amine oxide having formula $R^7R^8R^8N \rightarrow O$ (V),
an amine oxide having formula $R^7$—CO—NH—$R^9$—$R^8R^8N \rightarrow O$ (IV), or
a mixture or association thereof, wherein:

$R^7$ which is identical or different, is a linear or branched hydrocarbon group, preferably an alkyl group containing 3 to 30 carbon atoms, preferably 3 to 20 carbon atoms, $R^8$, which is identical or different, is a $C_1$-$C_3$ alkyl group, preferably a methyl group, and $R^9$, which is identical or different, is divalent linear or branched hydrocarbon group containing 1 to 6 carbon atoms, optionally substituted with a hydroxyl group, preferably a group of formula —$CH_2$—$CH_2$—$CH_2$— or —$CH_2$—$CHOH$—$CH_2$—.

The alkaline composition preferably has a pH (1% solution in water) in the range of from 8 to 13.5.

The alkaline composition may if desired contain other components such as adjuvants (for example crop oils, wetters, stickers, foaming agents and marking agents) and other active agents. Examples of complementary active agents which may be used include at least one selected from the group consisting of fungicides, insecticides and herbicides. Specific examples of additional active agents which may be present in the alkaline composition may comprise at least one selected from 2,4D, amitrole, ammonium sulphate, atrazine, carfentrazone, chlorsulfuron, dicamba, diuron, MCPA, metolachor, metribuzin, metsulfuron, oryzalin, oxyfluorfen, pendamethalin, picloram, simazine, terbutryne, triallate, triasulfuron, triclopyr and trifluralin.

The method of the invention involves addition of glyphosate acid to a dilute alkaline composition in a spray tank. Generally the alkaline composition will be diluted with water in the spray tank before the addition of glyphosate acid to the diluted alkaline composition. The glyphosate acid may be added as a concentrate or alternatively the glyphosate acid concentrate is dispersed in water prior to mixing with the alkaline composition in the spray tank.

In this embodiment the aqueous dispersion of the glyphosate acid may be formed from the glyphosate acid concentrate in a separate vessel and then added to the tank or it may be formed in or during addition to the spray tank. In general the glyphosate will be mixed with water and this may be achieved by stirring or agitating the glyphosate acid concentrate in water or by the impact of a stream of water on solid glyphosate acid concentrate.

The aqueous dispersion of glyphosate need not be a particularly stable dispersion as it may be added to the dilute alkaline composition within the spray tank within a short period. For example, the dispersion may be added immediately after it is formed to the diluted alkaline composition. A dispersion in water may therefore be suitable if it would otherwise settle within a short period of say 1 minute. Indeed the dispersion may be maintained entirely by the turbulence or mixing prior to addition to the spray tank.

An aqueous dispersion may be achieved by adding the glyphosate acid concentrate to a bucket of water and stirring with a stick, paddle or agitator, or by adding the glyphosate acid concentrate to a mixing vessel for vigorous agitation with water. The mixing vessel may provide mixing using a vortex of the diluent (typically water). A suitable mixing vessel for vortex mixing is available from Hardi Industries under the trade mark "Granni Pot" Chemical Indicator or from Gold Acres of St Arnaud, Victoria, Australia under the name of a Chemical Induction Hopper. The aqueous dispersion may also be achieved by adding solid particulate glyphosate acid concentrate to a perforated container such as a filter container located on or over the spray tank, and flushing the glyphosate through the perforations with a charge of water directed into the perforated container. In a particularly preferred embodiment the method of the invention involves placing solid particulate glyphosate acid concentrate in a container having perforations and dispersing the glyphosate acid in water by impacting the concentrate with a stream of water and draining the water from the perforated container into the spray tank. It is even more preferred in this embodiment that the water drains from the perforated container into the spray tank wherein the spray tank contains the alkaline composition optionally diluted with water.

The alkaline composition is preferably diluted with water in the spray tank.

For example the spray tank may be charged with an initial charge of water and alkaline composition and an aqueous dispersion of the glyphosate acid then added.

Accordingly in a particularly preferred embodiment of the invention we provide a method of preparing a spray tank composition of glyphosate comprising:

(a) providing an initial change of water to the spray tank, which initial charge of water may, for example, provide ¼ to ¾ of the total spray water volume and preferably approximately ½ of the total spray water volume;

(b) adding the alkali composition to the initial change of water to provide a diluted alkaline composition;

(c) dispersing solid particulate glyphosate acid concentrate in water;

(d) mixing the aqueous dispersion of glyphosate acid with the diluted alkaline composition; and (e) optionally adding more water to provide the desired volume.

The aqueous dispersion of glyphosate acid is preferably added to the alkaline composition (which is preferably diluted with water) having a pH of in the range of 7.5 to 10.5.

The volume of diluted herbicidal composition formed in the spray tank in accordance with the method of the invention is preferably in the range of from 50 to 20,000 litres, more preferably from 100 to 10,000 litres and most preferably from 400 to 5,000 litres.

The pH of the spray liquor after the combination of the compositions and dilution with water is preferably in the range 3.5 to 7 and more preferably from 4 to 6.0.

In the case of some amines including alkyl amines such as fatty amines (eg tallowamines) there is an advantage in working at lower pH values of for example from 2 to 5.5 and most preferably at about 2.

The process of the invention may further comprise the steps of preparing the glyphosate acid concentrate composition, transporting the glyphosate acid concentrate composition and forming a spray tank composition as hereinabove described. The spray tank composition will typically be prepared within several days of use and typically within a day of use whereas the glyphosate acid concentrate is stable for many months of storage and transport and allows diluents and solvents to be significantly reduced when compared with conventional glyphosate (salt type) concentrates.

The concentration of glyphosate (acid equivalent) in the final spray tank composition is preferably in the range 0.01% to 9.0% by weight, more preferably in the range 0.4 to 4% by weight and most preferably in the range 0.4 to 3% by weight.

The two pack system in accordance with the invention comprises a first pack containing the alkaline composition and a second pack containing the glyphosate concentrate as hereinbefore described. The two packs contain amounts of the respective glyphosate and alkaline component to provide at least 80% (based on glyphosate acid) of the glyphosate as water soluble glyphosate salt.

The two pack system may comprise instructions for mixing the packs of the system in accordance with the above described method steps.

In one preference, the ratio of glyphosate-synergising surfactant (in the first pack) to glyphosate (acid equivalent) in the second pack is in the range of from 1:1 to 1:20 for the active component of the adjuvant and more preferably 1:1 to 1:14. Typically the active surfactant component of the adjuvant is present in a diluent so that the ratio of formulated glyphosate-synergising surfactant to glyphosate is typically from 1:7 to 1:1 and preferably 1:3 to 1:4.

In one preference the first pack comprises alkaline material and glyphosate synergising surfactant.

Preferably the range of water in the first pack is less than 70% and preferably less that 50%.

In one preference the glyphosate synergising surfactant has a low aquatic animal toxicity.

In another preference the glyphosate synergising surfactant is an ethoxylated tallow amine.

Preferably the pH of liquor in the first pack is less than 13 and more preferably less than 12.

In one preference the alkaline material is monoethanolamine.

The contents of the two packs are typically combined in accordance with the above-described method.

Typically the molar ratio of glyphosate acid to alkaline component of the alkaline composition is in the range of from 6:1:1:2, preferably 0.8:1 to 1:1.2 and more preferably from 1:1.05 to 1:1.2.

In the case of alkyl amines including fatty amines such as tallowamine we have surprisingly found that a ratio as low as from 6:1 to 1:1.2, (such as from 6:1 to 1:1 or ^:1 to 1.2:1) is sufficient to solubilise the glyphosate and provide a useful product of high activity.

The invention will now be described with reference to a number of examples which are provided for the purpose of further understanding embodiments of the invention but are not intended to limit the scope or applicability of the invention to the specific examples.

EXAMPLES

Compositions and methods used in the examples, in particular the results of efficacy trials are described with reference to the attached drawings.

In the drawings:

FIG. 1 is a graph comparing the efficacy on ryegrass of a two pack glyphosate system of the invention of Example 1 with a commercial glyphosate herbicide formulation at various application rates.

FIG. 2 is a graph comparing the efficacy on oats of a two pack glyphosate system of the invention of Example 2 with a commercial glyphosate herbicidal formulation at various application rates.

FIG. 3 is a graph comparing the field efficacy on ryegrass of a two pack glyphosate system of the invention with a commercial glyphosate formulation at various application rates as described in Example 3.

Example 1

This example compares the bioefficacy of a 2 Pack glyphosate herbicide of the invention with a commercial glyphosate standard.
Method
Plant Propagation Annual ryegrass (*Lolium rigidum*) seeds (5/pot) were sown to a depth of 10 mm in 10 cm diameter pots filled with potting mix (Australian Standard 3743) that had been amended with macro and micronutrients for optimal growth.

One week after seedling emergence, seedlings were thinned for uniform size to one seedling per pot. Plants were grown in a temperature-controlled greenhouse (14° C.-25° C.) for 14 days then outdoors for 20 days prior to spray application to more closely simulate field conditions. After the application of herbicides the pots were returned to the greenhouse for an additional 14 days before plants were assessed for fresh weight.
Preparation of 2 Packs Herbicide Approximately 13 L of water was added to each of five 20 litre ("L") plastic buckets (Table 1). Pack 1 was made by taking 37.5 parts monoethanolamine ("MEA") and 25.3 parts of a cocobetaine surfactant called Empigen BB from Huntsman Chemical Company Australia. Pack 1 was also called the Alkaline-Surfactant Blend in this and later examples. Pack 1 was added to the water at the rates given in Table 1.

Glyphosate acid technical material with a purity of 95% and a particle size smaller than 1 mm (Pack 2) was then added to the buckets at the rates given in Table 1 and stirred with a plastic paddle until all the acid disappeared. This took 3-5 minutes at the higher concentrations.

1.3 L of each mix was then transferred to a 6 L spray canister and pressurized using compressed air.

TABLE 1

Mixing ratios of Alkali Surfactant Blend (Pack 1), glyphosate acid (Pack 2) and water and equivalent rate of glyphosate applied per hectare.

| Glyphosate Rate g ai/ha | Glyphosate concentration g ai/L | Pack 1 - Alkali-Surfactant blend ml/bucket | Pack 2- Glyphosate acid g/bucket | Water L/bucket |
|---|---|---|---|---|
| 45 | 0.70 | 5.79 | 9.62 | 12.99 |
| 90 | 1.41 | 11.58 | 19.24 | 12.99 |
| 180 | 2.81 | 23.17 | 38.49 | 12.98 |
| 360 | 5.63 | 46.34 | 76.97 | 12.95 |
| 450 | 7.03 | 57.92 | 96.22 | 12.94 |

NB ai = active ingredient measured as the pure acid.

Commercial Herbicide

A commercial glyphosate formulation Roundup Biactive™ was used as the commercial standard. Roundup Biactive™ herbicide is based on an isopropylamine (IPA) salt and contains a surfactant.

The commercial standard herbicide was added directly to the water in the spray canister at the required rate (Table 2) to match the concentration of pure glyphosate acid in the 2 Pack system described previously. The commercial standard was not mixed in a bucket.

TABLE 2

Mixing ratios of Roundup Biactive and water.

| Glyphosate Rate g ai/ha | Glyphosate concentration g ai/L | Roundup Biactive ™ concentration g/L | Roundup Biactive ™ ml/canister | Water L/canister |
|---|---|---|---|---|
| 45 | 0.70 | 360 | 2.54 | 1297.5 |
| 90 | 1.41 | 360 | 5.08 | 1294.9 |
| 180 | 2.81 | 360 | 10.16 | 1289.8 |
| 360 | 5.63 | 360 | 20.32 | 1279.7 |
| 450 | 7.03 | 360 | 25.39 | 1274.6 |

Herbicide Application

The annual ryegrass was at the early tillering stage (2 tillers) when sprayed with the herbicide treatments.

Herbicide formulations were applied using an enclosed laboratory track-sprayer fitted with three 110° flat fan nozzles ("Teejet"® XR11001-VS) spaced at 50 cm intervals across the boom. The boom moved along a fixed track at 6 km h−1, sprayed at a water volume of 64 L ha−1 with a pressure of 200 kPa.

There were eight replicates for each treatment.

Assessment

Seedlings were harvested 14 days after spray application by cutting foliage off at the base immediately prior to weighing on an "AND FX" 300 electronic balance (range 0-300 g).

Statistical Analysis

Data was analysed using a factorial design with two factors, glyphosate formulation (Formulation) and spray application rate (Rate). 95% least significant differences (LSD) were calculated for the mean of each treatment.

Results

Averaged across all rates there was no significant difference in the fresh weight of ryegrass treated with either of the formulations indicating that both formulations were of equal efficacy (Table 3). As expected there was a highly significant effect of application rate. There was no interaction between Rate and Formulation.

TABLE 3

Statistic analysis data for fresh weight of annual ryegrass plants at harvest.

| FACTOR | Prob (F) | LSD |
|---|---|---|
| Formulation | 0.71 | NS |
| Rate | 0.0001 | 0.43 g/plant |
| Formulation × Rate | 0.10 | NS |

NS = not significant (P < 0.05).
LSD = least significant difference (P = 0.05)

Raw data and means for fresh weight of annual ryegrass at harvest are tabled (Table 4) and graphed (FIG. 1).

TABLE 4

Fresh weight (g/plant) of plants harvested after treatment with two glyphosate formulations. Mean Rate data in the same column or Mean Formulation data in the same row that are followed by the same letter are not significantly different (P < 0.05).

| Glyphosate application rate g ai/ha | 2 Pack System | Roundup Biactive ™ | Rate Mean |
|---|---|---|---|
| 0 | 14.1 | 14.1 | |
| 45 | 12.9 | 12.4 | 12.6 e |
| 90 | 9.77 | 10.1 | 9.94 d |
| 180 | 5.97 | 6.36 | 6.17 c |
| 360 | 2.55 | 2.00 | 2.28 b |
| 450 | 1.76 | 1.71 | 1.74 a |
| Formulation Mean (not including the 0 g ai/ha rate) | 6.58 a | 6.53 a | |

Example 2

This example compares the herbicidal activity of a 2 Pack glyphosate system in accordance with the invention with commercial glyphosate standards on canola and oats.

Method

Plant Propagation

Oat (*Avena sativa*) and canola (*Brassica napus*) seeds (3/pot) were sown to a depth of 15 mm for the oats and 3 mm for the canola in 10 cm diameter pots filled with potting mix (Australian Standard 3743) that had been amended with macro and micronutrients for optimal growth.

One week after seedling emergence, seedlings were thinned for uniform size to one seedling per pot. Plants were grown in a temperature-controlled greenhouse (14° C.-25° C.) for 14 days then outdoors for 10 days prior to spray application to more closely simulate field conditions. After the application of herbicides the pots were returned to the greenhouse for an additional 14 days before plants were assessed for fresh weight.

2 Pack Herbicide Preparation

Approximately 13 L of water was added to seven 20 L plastic buckets (Table 5). A blend of 37.5 parts MEA and 25.3 parts of the cocobetain surfactant Empigen BB was made to form the Alkali Surfactant Blend (Pack 1). Pack 1 was then added to the water at the rates given in Table 5. Glyphosate acid (Pack 2) with a purity of 95% was then added to the buckets at the rates given in Table 5 and stirred with a plastic paddle until all the acid disappeared. This took 3-5 minutes at the higher concentrations.

1.3 L of each mix was then transferred to a 6 L spray canister and pressurized using compressed air.

TABLE 5

Mixing ratios of Alkali Surfactant Blend (Pack 1), glyphosate acid (Pack 2) and water at an equivalent rate of glyphosate applied per hectare. NB ai = active ingredient measured as the pure acid.

| Glyphosate Rate g ai/ha | Glyphosate concentration g ai/L | Pack 1 - Alkali-Surfactant Blend ml/bucket | Pack 2 - Glyphosate acid g/bucket | Water L/bucket |
|---|---|---|---|---|
| 30 | 0.47 | 3.86 | 6.41 | 13.00 |
| 60 | 0.94 | 7.72 | 12.83 | 12.99 |
| 90 | 1.41 | 11.58 | 19.24 | 12.99 |
| 120 | 1.88 | 15.45 | 25.66 | 12.98 |
| 180 | 2.81 | 23.17 | 38.49 | 12.98 |
| 240 | 3.75 | 30.89 | 51.32 | 12.97 |
| 450 | 7.03 | 57.92 | 96.22 | 12.94 |

Commercial Herbicides

Two commercial glyphosate formulations Roundup Biactive™ brand and Macphersons® Glyphosate 450 SL brand were used as commercial standards. Macphersons® Glyphosate 450SL is based on the MEA salt. Roundup Biactive™ is based on an IPA salt.

The commercial standard herbicides were added directly to the water in the spray canister at the required rate to match the concentration of pure glyphosate acid in the 2 Pack system described above (Table 6 and 7). The commercial standards were not mixed in a bucket.

"Roundup Biactive"™

TABLE 6

Mixing ratios of "Roundup Biactive" ™ and water.

| Glyphosate Rate g ai/ha | Glyphosate concentration g ai/L | Roundup Biactive ™ concentration g/L | Roundup Biactive ™ ml/canister | Water L/canister |
|---|---|---|---|---|
| 30 | 0.47 | 360 | 1.69 | 1298.3 |
| 60 | 0.94 | 360 | 3.39 | 1296.6 |
| 90 | 1.41 | 360 | 5.08 | 1294.9 |
| 120 | 1.88 | 360 | 6.77 | 1293.2 |
| 180 | 2.81 | 360 | 10.16 | 1289.8 |
| 240 | 3.75 | 360 | 13.54 | 1286.5 |
| 450 | 7.03 | 360 | 25.39 | 1274.6 |

"Macphersons"® Glyphosate 450 SL

TABLE 7

Mixing ratios of "Macphersons" ® Glyphosate 450SL and water.

| Glyphosate Rate g ai/ha | Glyphosate concentration g ai/L | Macphersons® Glyphosate 450SL concentration g/L | Macphersons® Glyphosate 450SL ml/canister | Water L/ canister |
|---|---|---|---|---|
| 30 | 0.47 | 450 | 1.35 | 1298.6 |
| 60 | 0.94 | 450 | 2.71 | 1297.3 |
| 90 | 1.41 | 450 | 4.06 | 1295.9 |
| 120 | 1.88 | 450 | 5.42 | 1294.6 |
| 180 | 2.81 | 450 | 8.13 | 1291.9 |
| 240 | 3.75 | 360 | 13.54 | 1286.5 |
| 450 | 7.03 | 360 | 25.39 | 1274.6 |

Herbicide Application

Both the oats and the canola were at the three leaf stage when sprayed with the herbicide treatments.

Herbicide formulations were applied using an enclosed laboratory track-sprayer fitted with three 110° flat fan nozzles ("Teejet"® XR11001-VS brand) spaced at 50 cm intervals across the boom. The boom moved along a fixed track at 7.7 km h$^{-1}$, sprayed at a water volume of 50 L ha$^{-1}$ with a pressure of 200 kPa.

There were 8 replicates for each treatments.

Assessment

Seedlings were harvested 14 days after spray application by cutting foliage off at base immediately prior to weighing on an "AND FX" 300 electronic balance (range 0-300 g).

Statistical Analysis

Data was analysed using a factorial design with two factors, glyphosate formulation (Formulation) and spray application rate (Rate). 95% least significant differences (LSD) were calculated for the mean of each treatment.

Results

Oats

When the fresh weight of the oats was averaged across all rates there was no significant difference between the formulations indicating that the three formulations had equal efficacy (Table 8). As expected there was a highly significant effect of application rate. There was no interaction between Rate and Formulation.

TABLE 8

Statistic analysis data for fresh weight of oat plants at harvest.

| FACTOR | Prob (F) | LSD |
|---|---|---|
| Formulation | 0.39 | NS |
| Rate | 0.0001 | 0.39 g/plant |
| Formulation × Rate | 0.99 | NS |

NS = not significant (P < 0.05).

Raw data for fresh weight and means for oats at harvest are tabled (Table 9) and graphed in (FIG. 2).

TABLE 9

Fresh weight (g/plant) of oat plants harvested after treatment with various glyphosate formulations. Mean Rate data in the same column or Mean Formulation data in the same row that are followed by the same letter are not significantly different (P < 0.05).

| Glyphosate application rate g ai/ha | 2 Pack System | MacPhersons 450SL | Roundup Biactive ™ | Rate Mean |
|---|---|---|---|---|
| 0 | 6.11 | 6.11 | 6.11 | |
| 30 | 5.61 | 5.43 | 5.52 | 5.52 e |
| 60 | 4.26 | 4.17 | 4.48 | 4.30 d |
| 90 | 2.60 | 2.66 | 2.94 | 2.73 c |
| 120 | 2.02 | 1.76 | 1.95 | 1.91 b |
| 180 | 1.19 | 1.14 | 0.90 | 1.08 a |
| 240 | 1.08 | 0.79 | 0.94 | 0.94 a |
| 450 | 0.73 | 0.61 | 0.95 | 0.76 a |
| Formulation Mean (not including the 0 g ai/ha rate) | 2.50 a | 2.36 a | 2.53 a | |

Canola

When the fresh weight of the canola was averaged across all rates there was no significant difference between the formulations indicating that the three formulations had equal efficacy (Table 10). As seen with the oats there was a highly significant effect of application rate. There was no interaction between Rate and Formulation.

TABLE 10

Statistic analysis data for fresh weight of canola plants at harvest.

| FACTOR | Prob (F) | LSD |
|---|---|---|
| Formulation | 0.16 | NS |
| Rate | 0.0001 | 0.29 g/plant |
| Formulation × Rate | 0.88 | NS |

NS = not significant (P < 0.05).

Raw data for fresh weight and means for canola at harvest are tabled (Table 11).

TABLE 11

Fresh weight (g/plant) of oat plants harvested after treatment with various glyphosate formulations. Mean Rate data in the same column or Mean Formulation data in the same row that are followed by the same letter are not significantly different (P < 0.05).

| Glyphosate application rate g ai/ha | 2 Pack System | MacPhersons 450SL | Roundup Biactive ™ | Rate Mean |
|---|---|---|---|---|
| 0 | 7.22 | 7.22 | 7.22 | |
| 30 | 5.09 | 4.81 | 4.99 | 4.96 e |
| 60 | 3.13 | 2.74 | 2.69 | 2.86 d |
| 90 | 1.43 | 1.17 | 1.37 | 1.32 c |
| 120 | 1.15 | 0.92 | 0.67 | 0.91 b |
| 180 | 0.53 | 0.68 | 0.57 | 0.59 a |
| 240 | 0.54 | 0.52 | 0.48 | 0.51 a |
| 450 | 0.47 | 0.46 | 0.42 | 0.45 a |
| Formulation Mean (not including the 0 g ai/ha rate) | 1.76 a | 1.61 a | 1.60 a | |

Example 3

This example compares the field bioefficacy of a 2 Pack glyphosate herbicide made according to the invention with a commercial glyphosate standard on annual ryegrass.

Method

Site Details

A field trial site was selected for uniformity of annual ryegrass (*Lolium rigidum*) near Werribee, Victoria, Australia. The weeds were at the late tillering stage (Zadocks GS 25-29)

and were growing vigorously. Soil moisture conditions were optimum for plant growth.

The site was sprayed on the 6 Sep. 2005, when wind conditions were slight (<5 kph).

Plots were 2 m×15 m with a 0.5 m buffer between each plot.

Mixing Tank Details

The mixing tank was a 200 L, wide mouth (mouth was 20 cm diameter) plastic tank with a diameter of approximately 65 cm and height 60 cm.

2 Pack Herbicide Preparation

70 L of water was added to the 200 L tank. A blend was made of 37 parts MEA and 25 parts of the cocobetaine surfactant Empigen BB to form the Alkali Surfactant Blend (Pack 1). The Alkali Surfactant Blend was then added to the water at one of the rates given in Table 12. A plastic mesh container insert (with holes approximately 4 mm diameter) was then placed into the mouth of the container and the corresponding amount of glyphosate acid (Pack 2) for the previously added Alkali Surfactant Blend (Table 12) was then added onto the mesh and washed into the container using a steady stream of water from a hose unto the total volume in the spray tank was 130 L. The tank had no agitation other than that caused by the action of the water stream leaving the hose while the additional 60 L of water was added.

A small plot experiment was done using a 1.3 L sample of the solution taken from the 200 L tank above. This sample was poured into a 6 L pressurised spray canister. After the 1.3 L of solution was transferred to the 6 L spray canister the canister was pressurized using compressed air.

This process was repeated for each of the spray application rates given in Table 12.

TABLE 12

Mixing ratios of Alkali Surfactant Blend (Pack 1), glyphosate acid (Pack 2) and water and equivalent rate of glyphosate applied per hectare. NB ai = active ingredient measured as the pure acid.

| Glyphosate Rate g ai/ha | Glyphosate concentration g ai/L | Pack 1 - Alkali-Surfactant Blend ml/spray tank | Pack 2 - Glyphosate acid g/spray tank | Water L/spray tank |
| --- | --- | --- | --- | --- |
| 45 | 0.70 | 57.9 | 96.2 | 129.9 |
| 90 | 1.41 | 115.8 | 192.4 | 129.9 |
| 180 | 2.81 | 231.7 | 384.9 | 129.8 |
| 360 | 5.63 | 463.4 | 769.7 | 129.5 |
| 450 | 7.03 | 579.2 | 962.2 | 129.4 |

Commercial Herbicide

A commercial glyphosate formulation Roundup Biactive™ was used as the commercial standard.

The commercial standard herbicide was added directly to the water in the spray canister at the required rate to match the concentration of pure glyphosate acid in the 2 Pack system described above. The commercial standard was not premixed in a larger container (Table 13).

"Roundup Biactive"™

TABLE 13

Mixing ratios of "Roundup Biactive" ™ and water.

| Glyphosate Rate g ai/ha | Glyphosate concentration g ai/L | Roundup Biactive" ™ concentration g/L | Roundup Biactive ™ ml/canister | Water L/ canister |
| --- | --- | --- | --- | --- |
| 45 | 0.71 | 360 | 2.54 | 1297.5 |
| 90 | 1.41 | 360 | 5.08 | 1294.9 |
| 180 | 2.81 | 360 | 10.16 | 1289.8 |
| 360 | 5.62 | 360 | 20.32 | 1279.7 |
| 450 | 7.03 | 360 | 25.39 | 1274.6 |

Herbicide Application

Herbicide formulations were applied using a hand held boom fitted with three 110° flat fan nozzles ("Teejet"® XR11001-VS) spaced at 50 cm intervals across the boom. The boom was moved along the plots at 6 km h$^{-1}$ and sprayed at a water volume of 64 L ha$^{-1}$ with a pressure of 200 kPa.

There were five replicates for each treatment.

Assessment

Weed counts were taken using 10×0.1 m$^2$ quadrants per replicate, 28 days after treatment.

Statistical Analysis

Data was analysed using a factorial design with two factors, glyphosate formulation (Formulation) and spray application rate (Rate). 95% least significant differences (LSD) were calculated for the mean of each treatment.

Results

Averaged across all rates there was no significant difference in the density of annual ryegrass between the formulations indicating that the two formulations had equal efficacy (Table 14). There was a highly significant effect of application rate. There was no interaction between Rate and Formulation.

TABLE 14

Statistic analysis data for the density of annual ryegrass plants. NS = not significant (P < 0.05).

| FACTOR | Prob (F) | LSD |
| --- | --- | --- |
| Formulation | 0.52 | NS |
| Rate | 0.0001 | 5.8 plants/m2 |
| Formulation × Rate | 0.68 | NS |

Raw data for the weed counts is tabled (Table 15) and graphed in (FIG. 3).

TABLE 15

Annual ryegrass density (plant/m$^2$) after treatment with two glyphosate formulations. Mean Rate data in the same column or Mean Formulation data in the same row that are followed by the same letter are not significantly different (P < 0.05).

| Glyphosate application rate g ai/ha | 2 Pack System | Roundup Biactive ™ | Rate Mean |
| --- | --- | --- | --- |
| 0 | 86.2 | 86.2 | |
| 45 | 77.4 | 71.6 | 74.5 d |
| 90 | 24.2 | 26.8 | 25.5 c |
| 180 | 9.6 | 8.8 | 9.2 b |
| 360 | 5.8 | 3.8 | 4.8 ab |
| 450 | 0.6 | 0.8 | 0.7 a |
| Formulation Mean (not including 0 g ai/ha) | 23.5 a | 22.4 a | |

Example 4

This example trials the mixing of a two pack system of the invention in a 1000 L commercial spray tank without plastic mesh insert.
Method
Spray Tank Details
A commercial "Silvan" Trailing Boom Spray fitted with a 1000 L tank was used for this experiment. The boom was 10 m wide.
Glyphosate Technical Material
The glyphosate material used was glyphosate acid (purity 95%) with a particle size where 95% can pass through a 1.2 mm sieve.
Addition
The spray tank was filled with 900 L of water. The recirculation or agitation system was driven by a power take off ("PTO") from the tractor. The recirculation system consisted of a wet boom, submerged at the base of the tank with outlets to one side of the tank's midline. This resulted in approximately 75% of the base of the tank on the same side as the jet outlets being swept by water. This is acceptable agitation by commercial spray boom standards.

With the PTO operating, a blend made from 0.979 kg of the surfactant Empigen BB and 1.57 kg of the monoethanolamine was poured into the tank and allowed to disperse for one minute.

4.26 kg of glyphosate acid was then tipped into the water. The glyphosate acid could be seen stuck to the base and sides of the tank and was not removed by the agitation of the water.

Five minutes after the addition of the glyphosate there was still some glyphosate acid adhering to surfaces but almost all disappeared over the next 5 minutes.

Although the time taken to completely dissolve was commercially feasible a product would ideally have a shorter dissolution time, ideally 3-5 minutes.

Example 5

This example describes a process of mixing a two pack glyphosate in a system in accordance with the invention, where one pack is a premilled glyphosate acid (particle size less than 0.5 mm), in a 1000 L commercial spray tank without plastic mesh insert.
Method
Spray Tank Details
A commercial "Silvan" brand Trailing Boom Spray fitted with a 1000 L tank was use for this experiment. The boom was 10 m wide.
Glyphosate Technical Material
Glyphosate acid (purity 95%) with a particle size where 95% can pass through a 0.5 mm sieve.
Addition
The spray tank was filled with 900 L of water. The recirculation or agitation system was driven by a PTO from the tractor. The recirculation system consisted of a wet boom at the base of the tank with outlets to one side of the tank's midline. This resulted in approximately 75% of the base of the tank on the same side as the jet outlets being swept by water. This is adequate agitation by commercial spray boom standards.

With the PTO operating, a blend made from 0.979 kg of the surfactant Empigen BB and 1.57 kg of the monoethanolamine was poured into the tank and allowed to disperse for one minute.

4.26 kg of the milled glyphosate acid was tipped into the water. As with the unmilled glyphosate acid the milled acid could be seen stuck to the base and sides of the tank and was dissolved over time by the agitation of the water.

Five minutes after addition there was still some glyphosate acid adhering to surfaces but by 10 minutes from addition all the acid had disappeared.

Example 6

This example describes mixing a two pack glyphosate system of the invention using a plastic mesh insert in a 1000 L commercial spray tank. The first pack (Alkali Surfactant Blend) contains a cocobetaine surfactant.
Method
Spray Tank Details
A commercial "Silvan" Trailing Boom Spray fitted with a 1000 L tank was use for this experiment. The boom was 10 m wide.
Glyphosate Technical Material
Glyphosate acid (purity 95%) with a particle size where 95% can pass through a 1.2 mm sieve but not through a 0.5 mm sieve.
Addition
The spray tank was filled with 900 L of water. The recirculation or agitation system was driven by a PTO from the tractor. The recirculation system consisted of a wet boom at the base of the tank with outlets to one side of the tank's midline. This resulted in approximately 75% of the base of the tank on the same side as the jet outlets being swept by water. This is adequate agitation by commercial spray boom standards.

A blend made from 0.979 kg of the surfactant Empigen BB, a cocobetaine surfactant, and 1.57 kg of the monoethanolamine (MEA) was poured into the tank and allowed to disperse for one minute. A sample of water was collected and analysed for pH.

A plastic mesh insert with holes of 3-4 mm diameter was fitted into the mouth of the tank and 4.26 kg of glyphosate acid was tipped into the insert. A low pressure hose was used to wash the acid through the mesh over a period of 1-2 minutes. Immediately after the mesh was empty it was removed and the water was inspected for evidence that the acid was not dissolved.
Results
There was no evidence of undissolved acid in the tank.

A sample of water was then taken and analysed for pH. The pH of the water taken from the tap and used to fill the tank was 7.3 and this increased to 9.9 with the addition of the alkali. The addition of the acid reduced this to 4.8, within the desirable range for glyphosate.

TABLE 16 pH of water at various stages of addition of ingredients.

| | pH |
|---|---|
| Water from tap | 7.3 |
| Water after addition of Alkali Surfactant Blend | 9.9 |
| Water after addition of Alkali Surfactant Blend and Glyphosate | 4.8 |

Example 7

This example compares field bioefficacy of a 2 Pack glyphosate herbicide in accordance with the invention with a commercial glyphosate standard on annual ryegrass, capeweed and barley grass.

Method

Site Details

A field trial site was selected for uniformity of annual ryegrass (*Lolium rigidum*), capeweed (*Arctotheca calendula*) and barley grass (*Hordeum leporinum*) near Ballarat, Victoria, Australia. The capeweed was flowering and the barley grass and annual ryegrass were just coming out in head and all were growing vigorously. Soil moisture conditions were optimum for plant growth.

The site was sprayed on the 16 Dec. 2005 when wind conditions were slight (<5 kph).

Plots were 10 m×100 m with a 10 m buffer between each plot. There were four replicates for each treatment.

Spray Solution

The spray solution in this example was that described in Example 6. The commercial standard was Roundup CT® glyphosate herbicide composition 450 g glyphosate ai/L which was added directly to the tank to give a 4.47 g ai/L concentration identical to that of the 2 Pack system.

The herbicide solutions were sprayed at 100 L/ha to deliver 447 g ai/ha.

Assessment

Plots were assessed visually for brown out seven days and 28 days after spraying. Brown out is an estimation of the proportion of plants that are dead or the proportion of an individual plant that has turned yellow or brown in response to the damage caused by the glyphosate herbicide.

Results

Annual Ryegrass

The two formulations were identical in their rate of brown out or the rate at which they killed annual ryegrass (Table 17).

TABLE 17

Annual ryegrass mean percent brown out 7 and 28 days after spraying with 450 g glyphosate acid/ha. Data in the same column and followed by the same letter and are not significantly different ($P < 0.05$).

| Treatment | Brown out (%) 7 Days | Brown Out (%) 28 days |
|---|---|---|
| Control | 0 | 0 |
| 2 Pack | 42 a | 99 a |
| Roundup CT | 37 a | 98 a |
| LSD (P = 0.05) | 8 | 1.2 |

Barley Grass

The two formulations were identical in their rate of brown out or the rate at which they killed barley grass (Table 18).

TABLE 18

Barley grass mean percent brown out 7 and 28 days after spraying with 450 g glyphosate acid/ha. Data in the same column and followed by the same letter are not significantly different ($P < 0.05$).

| Treatment | Brown out (%) 7 Days | Brown Out (%) 28 days |
|---|---|---|
| Control | 0 | 0 |
| 2 Pack | 62 a | 99 a |
| Roundup CT | 57 a | 99 a |
| LSD (P = 0.05) | 11 | 1.1 |

Capeweed

The two formulations were statistically similar in their rate of brown out or the rate at which they killed capeweed (Table 19).

TABLE 19

Capeweed mean percent brown out 7 and 28 days after spraying with 450 g glyphosate acid/ha.

| Treatment | Brown out (%) 7 Days | Brown Out (%) 28 days |
|---|---|---|
| Control | 0 | 0 |
| 2 Pack | 32 a | 91 a |
| Roundup CT | 35 a | 89 a |
| LSD (P = 0.05) | 6 | 3.8 |

Data in the same column and followed by the same letter are not significantly different ($P < 0.05$).

Example 8

In this example four Alkali Surfactant Blends were formulated using the proportion of ingredients given in Table 20. The surfactants in this example included a cocobetaine, an alkyl polyglycoside/EDA alkoxylate blend, an alkyl polyglycoside and a tallow amine ethoxylate. Each of these formulations was allowed to settle at room temperature for 24 hours and was then observed for phase separation. None of these four formulations showed any sign of separation (Table 21).

Each of these Alkali Surfactant Blends was added to 800 ml of water in a 1 L glass container. Sufficient glyphosate acid was then added to give a typical field concentration of 4.5 g/L. The ratio of Alkali Surfactant Blend to glyphosate acid was one part Alkali Surfactant Blend to 1.66 parts glyphosate acid. Tank mixes were tested for pH of resultant solution and time taken to dissolve completely (rate of dissolution). All formulations passed both of these tests, with the acid dissolving in less than 3 minutes and the pH being less than 5 (Table 21).

TABLE 20

Compositions of four 2 Pack glyphosate formulations (Parts on a weight basis)

| | EUR25-1 | EUR25-2 | EUR25-3 | EUR25-4 |
|---|---|---|---|---|
| Glyphosate acid | 100 | 100 | 100 | 100 |
| Alkali | | | | |
| MEA | 37.5 | — | — | 37.5 |
| KOH | — | 35.6 | 35.6 | — |
| Surfactant | | | | |
| Empigen BB | 25.3 | — | — | — |
| Terwet 1215 | — | 25.3 | — | — |
| Terwet 3780 | — | — | — | 25.3 |
| Terwet 3001 | — | — | 25.3 | — |
| Water | — | 17.5 | 10.0 | — |

Ingredients
Empigen BB is a cocobetaine
Terwet 1215 is an alkyl polyglycoside/EDA alkoxylate blend
Terwet 3001 is an alkyl polyglycoside
Terwet 3780 is a tallow amine ethoxylate

TABLE 21

Performance tests on four Alkali Surfactant Blends.

| | EUR25-1 | EUR25-2 | EUR25-3 | EUR25-4 |
|---|---|---|---|---|
| Pack 1 stability | Stable, no separation | Stable, no separation | Stable, no separation | Stable, no separation |
| Tank mix | | | | |
| pH | 4.5 | 4.8 | 4.8 | 4.7 |
| Rate of dissolution | <2 minutes | <2 minutes | <2 minutes | <2 minutes |

Example 9

This example describes a bioefficacy comparison of a 2 Pack glyphosate system of the invention, made using an alternative betaine type surfactant, with commercial glyphosate standards on annual ryegrass and wild radish Introduction This example relates to a system of the invention containing a betaine (specifically a cocamidopropyl betaine) in the Alkali Surfactant Blend component.

Method

Plant Propagation

Wild radish (*Raphanus raphanistrum*) seeds (3/pot) were sown to 2 mm depth and annual ryegrass (*Lolium rigidum*) seeds (3/pot) were sown to a depth of 5 mm in 10 cm diameter pots filled with potting mix (Australian Standard 3743) that had been amended with macro and micronutrients for optimal growth.

One week after seedling emergence, seedlings were thinned for uniform size to one seedling per pot. Plants were grown in a temperature-controlled greenhouse (14° C.-25° C.) for 18 days for annual ryegrass and 14 days for wild radish then outdoors for 22 days for annual ryegrass and 16 days for wild radish prior to spray application to more closely simulate field conditions. After the application of herbicides the pots were returned to the greenhouse for an additional 14 days before plants were assessed for fresh weight.

2 Pack Herbicide Preparation

In this example the monoethanolamine and cocamidopropyl betaine (also know as alkyl amidopropyl betaine) surfactant and sold as Huntsman's Empigen BS/FA surfactant blend was made using 37.5 parts monoethanolamine to 25.3 parts of cocamidopropyl betaine (aqueous concentration 30%). This blend is called the Alkali Surfactant Blend.

Approximately 13 L of water was added to seven 20 L plastic buckets (Table 22). The Alkali Surfactant Blend of monoethanolamine and the cocamidopropyl betaine (Pack 1) was then added to the water at the rates given in the Table. Glyphosate acid (Pack 2) with a purity of 95% was then added to the buckets at the corresponding rates (Table 22) and stirred with a plastic paddle until all the acid disappeared. This took approximately 3 minutes at the higher concentrations.

1.3 L of each mix was then transferred to a 6 L spray canister and pressurized using compressed air.

TABLE 22

Mixing ratios of Alkali Surfactant Blend (Pack 1), glyphosate acid (Pack 2) and water and equivalent rate of glyphosate applied per hectare.

| Glyphosate Rate g ai/ha | Glyphosate concentration g ai/L | Pack 1 - Alkali-Surfactant blend (MEA-BS/FA) ml/bucket | Pack 2-Glyphosate acid g/bucket | Water L/bucket |
|---|---|---|---|---|
| 30 | 0.47 | 3.86 | 6.41 | 13.00 |
| 60 | 0.94 | 7.72 | 12.83 | 12.99 |
| 90 | 1.41 | 11.58 | 19.24 | 12.99 |
| 120 | 1.88 | 15.45 | 25.66 | 12.98 |
| 180 | 2.81 | 23.17 | 38.49 | 12.98 |
| 240 | 3.75 | 30.89 | 51.32 | 12.97 |
| 450 | 7.03 | 57.92 | 96.22 | 12.94 |

NB ai = active ingredient measured as the pure acid.
BS/FA = Huntsman's Empigen BS/FA Commercial Herbicides Two commercial glyphosate formulations Roundup Biactive (containing an isopropylamine salt of glyphosate) and Macphersons Glyphosate 450 SL (containing a monoethanolamine salt of glyphosate) were used as commercial standards.

The commercial standard herbicides were added directly to the water in the spray canister at the required rate to match the concentration of pure glyphosate acid in the 2 Pack system described above. See Table 23 for Roundup Biactive and Table 24 for Macphersons Glyphosate 450SL mixing ratios with water in the spray canister. The commercial standards were not mixed in a bucket.

Roundup Biactive

TABLE 23

Mixing ratios of Roundup Biactive and water.

| Glyphosate Rate g ai/ha | Glyphosate concentration g ai/L | Roundup Biactive concentration g/L | Roundup Biactive g/canister | Water L/canister |
|---|---|---|---|---|
| 30 | 0.469 | 360 | 1.69 | 1298.3 |
| 60 | 0.938 | 360 | 3.39 | 1296.6 |
| 90 | 1.41 | 360 | 5.08 | 1294.9 |
| 120 | 1.875 | 360 | 6.77 | 1293.2 |
| 180 | 2.81 | 360 | 10.16 | 1289.8 |
| 240 | 3.75 | 360 | 13.54 | 1286.5 |
| 450 | 7.03 | 360 | 25.39 | 1274.6 |

Macphersons Glyphosate 450 SL

TABLE 24

Mixing ratios of Macphersons Glyphosate 450SL and water.

| Glyphosate Rate g ai/ha | Glyphosate concentration g ai/L | Macphersons Glyphosate 450SL concentration g/L | Macphersons Glyphosate 450SL g/canister | Water L/canister |
|---|---|---|---|---|
| 30 | 0.469 | 450 | 1.35 | 1298.6 |
| 60 | 0.938 | 450 | 2.71 | 1297.3 |
| 90 | 1.41 | 450 | 4.06 | 1295.9 |
| 120 | 1.875 | 450 | 5.42 | 1294.6 |
| 180 | 2.81 | 450 | 8.13 | 1291.9 |
| 240 | 3.75 | 360 | 13.54 | 1286.5 |
| 450 | 7.03 | 360 | 25.39 | 1274.6 |

Herbicide Application

The annual ryegrass was at early tillering stage and the wild radish at the early rosette stage when sprayed with the herbicide treatments.

Herbicide formulations were applied using an enclosed laboratory track-sprayer fitted with three 110° flat fan nozzles (Teejet XR11001-VS) spaced at 50 cm intervals across the boom. The boom moved along a fixed track at 7.7 km h$^{-1}$, sprayed at a water volume of 50 L ha$^{-1}$ with a pressure of 200 kPa.

There were 8 replicates for each treatments.

Assessment

Seedlings were harvested 14 days after spray application by cutting foliage off at base immediately prior to weighing on an AND FX 300 electronic balance (range 0-300 g).

Statistical Analysis

Data was analysed using a factorial design with two factors, glyphosate formulation (Formulation) and spray application rate (Rate). 95% least significant differences (LSD) were calculated for the mean of each treatment.

Results

Annual Ryegrass

Averaged across all rates there was a significant difference between the formulations (Table 25). As expected there was a highly significant effect of application rate. There was a significant interaction between Formulation and Rate.

TABLE 25

Statistic analysis data for fresh weight of annual ryegrass plants at harvest.

| FACTOR | Prob (F) | LSD |
|---|---|---|
| Formulation | <0.01 | 0.09 |
| Rate | <0.01 | 0.08 |
| Formulation × Rate | <0.01 | 0.26 |

Mean data (8 replicates) for fresh weight at harvest is tabled (Table 26).

When the fresh weight of the annual ryegrass was averaged across all rates there was no significant difference between the 2 Pack system (containing a cocamidopropyl betaine surfactant) and Macphersons 450SL. However, in this experiment both of these formulations were more efficacious than Roundup Biactive (Table 26). As expected there was a highly significant effect of application rate.

There was a significant interaction between Formulation and Rate due largely to higher than expected fresh weight for plants treated with Roundup Biactive in the mid rate range of 90 to 180 g ai/ha.

TABLE 26

Mean fresh weight (g/plant) of annual ryegrass plants harvested after treatment with a 2 Pack System (which contains a cocamidopropyl betaine as the surfactant component) compared with commercial standards Macphersons 450SL and Roundup Biactive.

| Glyphosate application rate g ai/ha | 2 Pack System | MacPhersons 450SL | Roundup Biactive |
|---|---|---|---|
| 0 | 6.21 | 6.21 | 6.21 |
| 30 | 5.52 | 5.91 | 5.60 |
| 60 | 4.75 | 5.08 | 5.04 |
| 90 | 2.71 | 2.73 | 3.28 |
| 120 | 2.11 | 2.05 | 2.85 |
| 180 | 1.30 | 1.03 | 1.47 |
| 240 | 0.61 | 0.48 | 0.76 |
| 450 | 0.30 | 0.19 | 0.23 |
| Formulation Mean (not including 0 g ai/ha) | 2.47 a | 2.50 a | 2.75 b |

Mean data followed by the same letter are not significantly different (P < 0.05).

Wild Radish

Averaged across all rates there was a significant difference between the formulations (Table 27). As expected there was a highly significant effect of application rate. There was a significant interaction between Formulation and Rate.

TABLE 27

Statistic analysis data for fresh weight of wild radish plants at harvest.

| FACTOR | Prob (F) | LSD |
|---|---|---|
| Formulation | <0.01 | 0.08 |
| Rate | <0.01 | 0.17 |
| Formulation × Rate | <0.01 | 0.21 |

Mean data (eight replicates) for fresh weight at harvest is tabled (Table 25).

When the fresh weight of the wild radish was averaged across all rates there was no significant difference between the 2 Pack system (containing a cocamidobetaine surfactant) and Macphersons 450SL. However, as with the ryegrass, both of these formulations were more efficacious than Roundup Biactive (Table 28). As expected there was a highly significant effect of application rate.

There was a significant interaction between Formulation and Rate once again due largely to higher than expected harvested weights for wild radish plants treated with Roundup Biactive in the mid rate range of 90-180 g ai/ha.

TABLE 28

Mean fresh weight (g/plant) of wild radish plants harvested after treatment with a 2 Pack System (which contains a cocamidopropyl betaine as the surfactant component) compared with commercial standards Macphersons 450SL and Roundup Biactive.

| Glyphosate application rate g ai/ha | 2 Pack System | MacPhersons 450SL | Roundup Biactive |
|---|---|---|---|
| 0 | 7.25 | 7.25 | 7.25 |
| 30 | 5.90 | 6.40 | 6.36 |
| 60 | 4.94 | 5.33 | 5.48 |
| 90 | 4.14 | 4.21 | 4.48 |
| 120 | 3.35 | 3.39 | 3.68 |
| 180 | 2.38 | 2.20 | 3.07 |
| 240 | 1.41 | 1.17 | 1.46 |
| 450 | 0.27 | 0.22 | 0.26 |
| Average | 3.20 a | 3.27 a | 3.54 b |

Mean data followed by the same letter are not significantly different (P < 0.05).

Experiment 10

Bioefficacy comparison on annual ryegrass of a 2 Pack glyphosate system using a cocamidopropyl betaine (also know as alkyl amidopropyl betaine) and triethanolamine glyphosate salt with commercial glyphosate standards.

Introduction

Triethanolamine is an alternative alkali to monoethanolamine. Cocamidopropyl betaine is a surfactant option that has been used in Example 9.

Method

Plant Propagation

Annual ryegrass (*Lolium rigidum*) seeds (3/pot) were sown to a depth of 5 mm in 10 cm diameter pots filled with potting mix (Australian Standard 3743) that had been amended with macro and micronutrients for optimal growth.

One week after seedling emergence, seedlings were thinned for uniform size to one seedling per pot. Plants were grown in a temperature-controlled greenhouse (14° C.-25° C.) for 18 days then outdoors for 22 days prior to spray application to more closely simulate field conditions. After the application of herbicides the pots were returned to the greenhouse for an additional 14 days before plants were assessed by harvesting all foliage for fresh weight.

2 Pack Herbicide Preparation

In this example the triethanolamine-cocamidopropyl betaine surfactant blend was made using 91.6 parts triethanolamine to 25.3 parts cocamidopropyl betaine (aqueous concentration 30%) and is called the Alkali Surfactant Blend.

Approximately 13 L of water was added to seven 20 L plastic buckets. A blend of triethanolamine and the cocamidopropyl betaine (also know as alkyl amidopropyl betaine) surfactant sold as Huntsman's Empigen BS/FA (Pack 1) was then added to the water at the rates given in the Table 29. Glyphosate acid (Pack 2) with a purity of 95% was then added to the buckets at the corresponding rate (Table 29) and stirred with a plastic paddle until all the acid disappeared.

1.3 L of each mix was then transferred to a 6 L spray canister and pressurized using compressed air.

TABLE 29

Mixing ratios of the Alkali Surfactant Blend (Pack 1), glyphosate acid (Pack 2) and water and equivalent rate of glyphosate applied per hectare.

| Glyphosate Rate g ai/ha | Glyphosate concentration g ai/L | Pack 1 - Alkali-Surfactant blend (triethanolamine - BS/FA) ml/bucket | Pack 2- Glyphosate acid g/bucket | Water L/bucket |
|---|---|---|---|---|
| 30 | 0.47 | 3.86 | 6.41 | 13.00 |
| 60 | 0.94 | 7.72 | 12.83 | 12.99 |
| 90 | 1.41 | 11.58 | 19.24 | 12.99 |
| 120 | 1.88 | 15.45 | 25.66 | 12.98 |
| 180 | 2.81 | 23.17 | 38.49 | 12.98 |
| 240 | 3.75 | 30.89 | 51.32 | 12.97 |
| 450 | 7.03 | 57.92 | 96.22 | 12.94 |

NB ai = active ingredient measured as the pure acid.
BS/FA = Huntsman's Empigen BS/FA Commercial Herbicides Two commercial glyphosate formulations Roundup Biactive and Macphersons Glyphosate 450 SL were used as commercial standards.

The commercial standard herbicides were added directly to the water in the spray canister at the required rate to match the concentration of pure glyphosate acid in the 2 pack system described above. See Table 30 for Roundup Biactive and Table 31 for Macphersons Glyphosate 450SL mixing ratios with water in the spray canister. The commercial standards were not mixed in a bucket.

Roundup Biactive

TABLE 30

Mixing ratios of Roundup Biactive and water.

| Glyphosate Rate g ai/ha | Glyphosate concentration g ai/L | Roundup Biactive concentration g/L | Roundup Biactive g/canister | Water L/canister |
|---|---|---|---|---|
| 30 | 0.469 | 360 | 1.69 | 1298.3 |
| 60 | 0.938 | 360 | 3.39 | 1296.6 |
| 90 | 1.41 | 360 | 5.08 | 1294.9 |
| 120 | 1.875 | 360 | 6.77 | 1293.2 |
| 180 | 2.81 | 360 | 10.16 | 1289.8 |
| 240 | 3.75 | 360 | 13.54 | 1286.5 |
| 450 | 7.03 | 360 | 25.39 | 1274.6 |

Macphersons Glyphosate 450 SL

TABLE 31

Mixing ratios of Macphersons Glyphosate 450SL and water.

| Glyphosate Rate g ai/ha | Glyphosate concentration g ai/L | Macphersons Glyphosate 450SL concentration g/L | Macphersons Glyphosate 450SL g/canister | Water L/canister |
|---|---|---|---|---|
| 30 | 0.469 | 450 | 1.35 | 1298.6 |
| 60 | 0.938 | 450 | 2.71 | 1297.3 |
| 90 | 1.41 | 450 | 4.06 | 1295.9 |
| 120 | 1.875 | 450 | 5.42 | 1294.6 |
| 180 | 2.81 | 450 | 8.13 | 1291.9 |
| 240 | 3.75 | 360 | 13.54 | 1286.5 |
| 450 | 7.03 | 360 | 25.39 | 1274.6 |

Herbicide Application

The annual ryegrass was at early tillering stage when sprayed with the herbicide treatments.

Herbicide formulations were applied using an enclosed laboratory track-sprayer fitted with three 110° flat fan nozzles (Teejet XR11001-VS) spaced at 50 cm intervals across the boom. The boom moved along a fixed track at 7.7 km h$^{-1}$, sprayed at a water volume of 50 L ha$^{-1}$ with a pressure of 200 kPa.

There were 8 replicates for each treatments.

Assessment

Seedlings were harvested 14 days after spray application by cutting foliage off at base immediately prior to weighing on an AND FX 300 electronic balance (range 0-300 g).

Statistical Analysis

Data was analysed using a factorial design with two factors, glyphosate formulation (Formulation) and spray application rate (Rate). 95% least significant differences (LSD) were calculated for the mean of each treatment.

Results

Averaged across all rates there was a no significant difference between the formulations proving that the efficacy of the 2 Pack system containing a triethanolamine base and cocamidopropyl betaine surfactant and the commercial standards was similar (Table 32). As expected there was a highly significant effect of application rate.

TABLE 32

Statistic analysis data for fresh weight of annual ryegrass plants at harvest.

| FACTOR | Prob (F) | LSD |
|---|---|---|
| Formulation | NS | |
| Rate | <0.01 | 0.17 |
| Formulation × Rate | NS | |

NS = Not significantly different (P < 0.05).

Mean data (8 replicates) for fresh weight at harvest is tabled (Table 33).

TABLE 33

Mean Fresh weight (g/plant) of annual ryegrass plants harvested after treatment with a 2 Pack system (which contains a cocamidopropyl betaine as the surfactant component and triethanolamine as the alkali) with commercial standards Macphersons 450SL and Roundup Biactive.

| Glyphosate application rate g ai/ha | 2 Pack System | MacPhersons 450SL | Roundup Biactive |
|---|---|---|---|
| 0 | 6.41 | 6.41 | 6.41 |
| 30 | 5.79 | 5.73 | 5.67 |
| 60 | 4.83 | 4.87 | 4.82 |
| 90 | 2.63 | 2.55 | 2.59 |
| 120 | 2.17 | 2.29 | 2.23 |
| 180 | 1.32 | 1.34 | 1.33 |
| 240 | 0.64 | 0.64 | 0.63 |
| 450 | 0.30 | 0.31 | 0.30 |
| Means | 2.53 a | 2.53 a | 2.51 a |

Mean data followed by the same letter are not significantly different (P < 0.05).

Finally, it is understood that various other modifications and/or alterations may be made without departing from the spirit of the present invention as outlined herein.

The invention claimed is:

1. A method of preparing a spray tank mix of glyphosate for application to plants from a spray tank, the method comprising the steps of:
   (a) providing a two pack formulation system comprising (i) a pack of a glyphosate acid concentrate in the form of solid particulate material of particle size in the range 0.1 mm to 5 mm said concentrate composition comprising at least 80% by weight glyphosate acid and (ii) a pack of a water soluble alkaline composition comprising an alkanolamine and a surfactant;

(b) providing a spray tank for spray application to plants;
(c) diluting the alkaline composition with water in the spray tank to provide a diluted alkaline mixture comprising alkanolamine and surfactant;
(d) forming an aqueous dispersion of the particulate glyphosate acid concentrate by mixing;
(e) adding the mixed aqueous dispersion of particulate glyphosate acid to the dilute alkaline mixture to thereby react therewith and form an alkanolamine salt of glyphosate in situ in the spray tank; and
(f) optionally adding further water to the spray tank to provide the spray tank mix of alkanolamine salt of glyphosate for application to plants from the spray tank wherein the spray tank mix comprises in the range of from 0.1 to 9.0% by weight glyphosate salt based on glyphosate acid equivalent.

2. A method according to claim 1 wherein the concentrate comprising glyphosate acid is a solid particulate material of particle size in the range of from 0.1 mm to 2 mm.

3. A method according to claim 2 wherein the glyphosate acid concentrate is in the form of particles comprising less than 10% by weight water.

4. A method according to claim 1 wherein the alkaline composition has pH in the range of from 8 to 13.5.

5. A method according to claim 1 wherein the alkaline composition comprises at least one alkaline material selected from the group consisting of monoethanolamine, diethanolamine, triethanolamine, alkyl ethanolamine, alkyl diethanolamine and alkylamine ethoxylates.

6. A method according to claim 1 wherein the alkaline composition comprises one or more surfactants selected from the group consisting of alkylamine ethoxylates, cocobetaine, alkoxylated aliphaticamine, aliphaticpolyglucoside, alkylglycoside, aliphaticamine quaternary amines, aliphaticamine acetate, ethylene diamine ethoxylate, amphoteric surfactants, amine oxides, amphoacetates, cocobetaine and cocamidopropyl betaines.

7. A method according to claim 1 wherein the alkaline composition comprises at least one surfactant selected from the group consisting of:
(a) Betaine surfactant of formula IIa

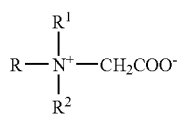

wherein R is $C_{12}$ to $C_{18}$ alkyl, $C_{12}$ to $C_{18}$ alkenyl, or alkylamidoalkyl, and $R^1$ and $R^2$ are each independently ($C_1$ to $C_6$) alkyl or hydroxyl ($C_1$ to $C_6$) alkyl;
wherein "alkylamidoalkyl" means a group according to formula III:

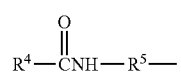

wherein $R^4$ is $C_1$ to $C_{30}$ alkyl or $C_1$ to $C_{30}$ alkenyl and $R^5$ is a $C_1$ to $C_6$ alkylenyl;
(b) Aliphatic amines and ethoxylated aliphatic or ethoxylated alkyl/fatty amines comprising at least one hydrocarbon group containing 12 to 18 carbon atoms, optionally polyalkoxylated; and (c) Amine oxide surfactant selected from group consisting of:
an amine oxide having formula $R^7R^8R^8N{\rightarrow}O$ (V),
an amine oxide having formula $R^7-CO-NH-R^9-R^8R^8N{\rightarrow}O$ (VI), or
a mixture or association thereof,
wherein:
$R^7$ is a linear or branched hydrocarbon group, an alkyl group containing 3 to 30 carbon atoms, preferably 3 to 20 carbon atoms,
$R^8$, which is identical or different, is a $C_1$-$C_3$ alkyl group, and
$R^9$ is divalent linear or branched hydrocarbon group containing 1 to 6 carbon atoms, optionally substituted with a hydroxyl group.

8. A method according to claim 5 wherein the glyphosate acid and alkaline material are mixed in a molar ratio of glyphosate acid:alkaline material in the range of 0.8 to 1 to 1 to 1.2.

9. A method according to claim 1 wherein the final volume of spray tank mixture is in the range of from 50 to 20,000 liters.

10. A method according to claim 1 wherein the glyphosate acid composition and alkaline composition are mixed to provide a pH in the spray tank mix of alkanolamine salt of glyphosate in the range of from 3.5 to 6.0.

11. A method according to claim 1 wherein the aqueous dispersion of the particulate glyphosate acid concentrate is prepared in a mixing vessel providing a vortex of water.

12. A method of preparing a spray tank mix of glyphosate for application to plants from a spray tank the method comprising the steps of:
(a) providing a two pack formulation system comprising
(i) a pack of a glyphosate acid concentrate in the form of solid particulate material having a particle size in the range of 0.1 to 2 mm and comprising less than 10% by weight water,
said concentrate composition comprising at least 80% by weight glyphosate acid, and
(ii) a pack of water soluble alkaline composition comprising ethanolamine and a surfactant;
(b) providing a spray tank for spray application to plants;
(c) diluting the alkaline composition with water in the spray tank to provide a diluted alkaline mixture comprising ethanolamine and surfactant;
(d) forming an aqueous dispersion of the particulate glyphosate acid concentrate by mixing;
(e) adding the mixed aqueous dispersion of particulate glyphosate acid to the dilute alkaline mixture to react with the alkaline mixture to form an ethanolamine salt of glyphosate in situ in the spray tank; and
(f) optionally adding further water to the spray tank;
to provide the spray tank mix of glyphosate for application to plants from a spray tank wherein the final volume of spray tank mixture is from 50 to 20,000 liters and comprises from 0.1 to 9.0% by weight glyphosate salt based on glyphosate acid equivalent.

13. A method according to claim 1 wherein the alkanolamine is ethanolamine.

14. A method of preparing a spray tank mix of glyphosate for application to plants from a spray tank, the method comprising the steps of:
(a) providing a two pack formulation system comprising (i) a pack of a glyphosate acid concentrate in the form of solid particulate material of a particle size in the range of 0.1 mm to 5 mm, said concentrate composition comprising at least 80% by wt. glyphosate acid and (ii) a pack of a water soluble alkaline composition comprising an alkanolamine and a betaine surfactant;

(b) providing a spray tank for spray application to plants;

(c) diluting the alkaline composition with water in the spray tank to provide a diluted alkaline mixture comprising alkanolamine and betaine surfactant;

(d) forming an aqueous dispersion of the particulate glyphosate acid concentrate with mixing;

(e) adding the mixed aqueous dispersion of particulate glyphosate acid to the dilute alkaline mixture to react therewith and form the alkanolamine salt of glyphosate in situ in the spray tank; and (f) optionally adding further water to the spray tank to provide the spray tank mix of alkanolamine salt of glyphosate for application to plants from the spray tank wherein the spray tank mix comprises in the range of from 0.1 to 9.0 wt. % glyphosate salt based on glyphosate acid equivalent.

15. A method according to claim 14 wherein the betaine surfactant is selected from the group consisting of alkylbetaine surfactants and alkylamidoalkylbetaine surfactants.

16. A method according to claim 6 further comprising preparing a kit comprising a first pack of the glyphosate acid concentrate in the form of particles comprising at least 80% by weight glyphosate acid based on the weight of glyphosate acid concentrate, and a second pack comprising alkanolamine and said one or more surfactants, and transporting the kit to the site of use.

* * * * *